US009101714B2

(12) United States Patent
Miyazaki et al.

(10) Patent No.: US 9,101,714 B2
(45) Date of Patent: Aug. 11, 2015

(54) FLUID INJECTION SYSTEM

(71) Applicant: Seiko Epson Corporation, Tokyo (JP)

(72) Inventors: Hajime Miyazaki, Matsumoto (JP);
Atsuya Hirabayashi, Chino (JP);
Yasuharu Hashimoto, Kamiina-gun (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/939,348

(22) Filed: Jul. 11, 2013

(65) Prior Publication Data

US 2013/0296775 A1    Nov. 7, 2013

Related U.S. Application Data

(63) Continuation of application No. 13/050,184, filed on Mar. 17, 2011, now Pat. No. 8,506,523.

(30) Foreign Application Priority Data

Mar. 25, 2010   (JP) ................................. 2010-071024

(51) Int. Cl.
*A61M 31/00* (2006.01)
*A61M 5/172* (2006.01)
(Continued)

(52) U.S. Cl.
CPC .......... *A61M 5/1723* (2013.01); *A61M 5/14244* (2013.01); *A61M 5/168* (2013.01);
(Continued)

(58) Field of Classification Search
CPC ................. A61M 37/0015; A61M 2037/0023; A61M 2209/088; A61M 2230/201; A61M 5/14248; A61M 2005/14268; A61M 2205/3334; A61M 2205/502; A61M 5/16831; A61M 5/172; A61B 5/14532; A61B 5/681; A61B 5/7465; F04B 19/006; Y10S 977/906
USPC ........................................................ 604/66
See application file for complete search history.

(56) References Cited

U.S. PATENT DOCUMENTS 3,949,388 A * 4/1976 Fuller ....................... 340/870.17
5,050,612 A * 9/1991 Matsumura ................... 600/483
(Continued)

FOREIGN PATENT DOCUMENTS

| CN | 101116756 | 6/2008 |
|---|---|---|
| JP | 2002-085556 | 3/2002 |

(Continued)

OTHER PUBLICATIONS

U.S. Appl. No. 13/050,184, Dec. 27, 2011, Office Action.
(Continued)

*Primary Examiner* — Nicholas Lucchesi
*Assistant Examiner* — Diva K Chander
(74) *Attorney, Agent, or Firm* — Workman Nydegger (57) ABSTRACT

A fluid injection system includes: a first apparatus which is attached to a human body and injects a fluid into the human body; and a second apparatus which is attached to a wrist of the human body and remotely controls the first apparatus, wherein the second apparatus includes an entry section accepting an entry of an operation command to the first apparatus and a first communicating section transmitting the operation command to the first apparatus, and the first apparatus includes a second communicating section receiving the operation command, a storing section storing the fluid, and a transporting section transporting the fluid from the storing section and injecting the fluid into the human body based on the operation command.

10 Claims, 3 Drawing Sheets

(51) Int. Cl.
*A61M 5/142* (2006.01)
*A61M 5/168* (2006.01)

(52) U.S. Cl.
CPC ....... *A61M5/16804* (2013.01); *A61M 2205/35* (2013.01); *A61M 2205/3569* (2013.01); *A61M 2205/3576* (2013.01); *A61M 2230/63* (2013.01)

(56) References Cited

U.S. PATENT DOCUMENTS

| | | | |
|---|---|---|---|
| 6,589,229 B1 * | 7/2003 | Connelly et al. | 604/890.1 |
| 7,901,383 B2 * | 3/2011 | Follman et al. | 604/187 |
| 2003/0212379 A1 | 11/2003 | Bylund et al. | |
| 2005/0027174 A1 * | 2/2005 | Benardot | 600/300 |
| 2006/0015058 A1 * | 1/2006 | Kellogg et al. | 604/22 |
| 2007/0040449 A1 | 2/2007 | Spurlin et al. | |
| 2007/0060869 A1 | 3/2007 | Tolle et al. | |
| 2007/0060870 A1 | 3/2007 | Tolle et al. | |
| 2007/0093786 A1 | 4/2007 | Goldsmith et al. | |
| 2007/0128060 A1 | 6/2007 | Miyazaki et al. | |
| 2007/0179534 A1 | 8/2007 | Firlik et al. | |
| 2008/0114292 A1 * | 5/2008 | Rasch-Menges et al. | 604/65 |
| 2008/0195045 A1 | 8/2008 | Lanigan | |
| 2009/0177142 A1 * | 7/2009 | Blomquist et al. | 604/66 |
| 2009/0227855 A1 | 9/2009 | Hill et al. | |
| 2009/0240193 A1 * | 9/2009 | Mensinger et al. | 604/66 |
| 2010/0201196 A1 | 8/2010 | Spurlin et al. | |
| 2011/0092882 A1 | 4/2011 | Firlik et al. | |
| 2012/0010562 A1 | 1/2012 | Hill et al. | |
| 2012/0091813 A1 | 4/2012 | Spurlin et al. | |

FOREIGN PATENT DOCUMENTS

| | | |
|---|---|---|
| JP | 2002-514932 | 5/2002 |
| JP | 2003-290345 | 10/2003 |
| JP | 2004-024699 | 1/2004 |
| JP | 2004-524869 | 8/2004 |
| JP | 2007-138775 | 6/2007 |
| JP | 2009-504323 | 2/2009 |
| JP | 2009-512516 | 3/2009 |
| JP | 2009-525828 | 7/2009 |
| JP | 2010-503515 | 4/2010 |
| WO | 93-14807 | 8/1993 |
| WO | 02-28454 | 4/2002 |
| WO | 2008-036658 | 3/2008 |
| WO | 2010-031059 | 3/2010 |

OTHER PUBLICATIONS

U.S. Appl. No. 13/050,184, Oct. 9, 2012, Final Office Action.
U.S. Appl. No. 13/050,184, Apr. 4, 2013, Notice of Allowance.

* cited by examiner

FLUID INJECTION SYSTEM

This application is a Continuation of U.S. patent application Ser. No. 13/050,184, filed Mar. 17, 2011, which claims priority to Japanese Patent Application No. 2010-071024, filed Mar. 25, 2010, which applications are expressly incorporated by reference herein.

BACKGROUND

1. Technical Field

The present invention relates to a fluid injection system which injects a fluid into a human body.

2. Related Art

In the past, there has been the technology related to a fluid injection apparatus which is attached to a human body and injects a fluid into the human body. With this fluid injection apparatus, it is possible to inject a fluid into the human body easily. JP-A-2007-138775 is an example of related art.

However, in the above technology, there is a need to expose the fluid injection apparatus by making an apparatus wearer get partially undressed in order to perform operation such as starting the injection of the fluid or stopping the injection. That is, the apparatus wearer has to get partially undressed in front of other people when operating the fluid injection apparatus while the apparatus wearer is out. This inflicts psychological suffering on the apparatus wearer who worries about attracting public attention, for example.

SUMMARY

An advantage of some aspects of the invention is to operate a fluid injection apparatus without making an apparatus wearer get partially undressed.

According to an aspect of the invention, there is provided a fluid injection system, including: a fluid injection apparatus which is attached to a human body and injects a fluid into the human body; and an operating apparatus which is attached to a wrist of the human body and remotely controls the fluid injection apparatus, wherein the operating apparatus includes an entry accepting section accepting an entry of an operation command to the fluid injection apparatus, and a first communicating section transmitting the operation command to the fluid injection apparatus, and the fluid injection apparatus includes a second communicating section receiving the operation command, a fluid storing section storing the fluid, and a fluid transporting section transporting the fluid from the fluid storing section and injecting the fluid into the human body based on the operation command.

The other features of the invention will be made clear by the descriptions of the present specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

The descriptions of the present specification and the accompanying drawings will explain at least the following matters.

That is, there is provided a fluid injection system, including: a fluid injection apparatus which is attached to a human body and injects a fluid into the human body; and an operating apparatus which is attached to a wrist of the human body and remotely controls the fluid injection apparatus, wherein the operating apparatus includes an entry accepting section accepting an entry of an operation command to the fluid injection apparatus, and a first communicating section transmitting the operation command to the fluid injection apparatus, and the fluid injection apparatus includes a second communicating section receiving the operation command, a fluid storing section storing the fluid, and a fluid transporting section transporting the fluid from the fluid storing section and injecting the fluid into the human body based on the operation command.

With such a fluid injection system, it is possible for an apparatus wearer of the fluid injection system to operate the fluid injection apparatus without getting partially undressed.

In such a fluid injection system, the operating apparatus includes a living body information detecting section detecting living body information of the human body and a living body information flow rate calculating section calculating the fluid flow rate of the fluid which is injected by the fluid injection apparatus based on the living body information, the first communicating section transmits data on the fluid flow rate calculated by the living body information flow rate calculating section to the fluid injection apparatus, the second communicating section receives the data on the fluid flow rate calculated by the living body information flow rate calculating section, and the fluid transporting section transports the fluid from the fluid storing section and injects the fluid into the human body based on the data on the fluid flow rate calculated by the living body information flow rate calculating section.

With such a fluid injection system, it is possible to calculate the transportation amount of fluid based on the living body information and thereby inject an appropriate amount of fluid into the apparatus wearer.

In such a fluid injection system, the operating apparatus includes an acceleration detecting section detecting the acceleration of the operating apparatus and an acceleration flow rate calculating section calculating the fluid flow rate based on the acceleration, the first communicating section transmits data on the fluid flow rate calculated by the acceleration flow rate calculating section to the fluid injection apparatus, the second communicating section receives the data on the fluid flow rate calculated by the acceleration flow rate calculating section, and the fluid transporting section transports the fluid from the fluid storing section and injects the fluid into the human body based on the data on the fluid flow rate calculated by the acceleration flow rate calculating section.

With such a fluid injection system, it is possible to calculate the transportation amount of fluid based on the exercise situation of the apparatus wearer and thereby inject an appropriate amount of fluid into the apparatus wearer.

In such a fluid injection system, the fluid injection apparatus includes a controller controlling the fluid transporting section and a second monitoring section monitoring the controller, and the operating apparatus includes a first monitoring section monitoring the controller and an alert issuing section issuing an alert when the first monitoring section or the second monitoring section detects an abnormality in the controller.

With such a fluid injection system, it is possible to inform the apparatus wearer of an abnormality without delay if an abnormality is detected in the controller of the fluid injection apparatus and improve the safety in use.

In such a fluid injection system, the fluid injection apparatus includes a transportation amount measuring section measuring the fluid flow rate of the fluid transported by the fluid transporting section, and the operating apparatus includes a pump abnormality determining section determining whether or not something is wrong with the fluid transporting section based on the operation command and the data on the fluid flow rate and an alarm sending section sending an alarm when the pump abnormality determining section determines that something is wrong with the fluid transporting section.

With such a fluid injection system, it is possible to inform the apparatus wearer of an abnormality without delay if something is wrong with the fluid transporting section of the fluid injection apparatus and improve the safety in use.

In such a fluid injection system, the operating apparatus includes a remaining amount calculating section calculating the remaining amount of fluid in the fluid storing section based on the transportation amount of fluid measured by the transportation amount measuring section and the amount of fluid originally stored in the fluid storing section and a display section displaying the remaining amount calculated by the remaining amount calculating section.

With such a fluid injection system, a person can check the remaining amount of fluid easily without getting partially undressed.

In such a fluid injection system, the fluid is a chemical which reduces the blood sugar level of the human body, the fluid injection apparatus includes a blood sugar level detecting section detecting the blood sugar level of the human body, and the operating apparatus includes a blood sugar level determining section which determines that the human body is in a state of hypoglycemia when the blood sugar level is less than a predetermined value and transmits an operation command to stop injection of the fluid to the fluid injection apparatus via the first communicating section.

With such a fluid injection system, even when the apparatus wearer becomes hypoglycemia, it is possible to stop injection of the chemical and thereby use the apparatus safely.

In such a fluid injection system, the blood sugar level determining section determines that the human body is in a state of hyperglycemia when the blood sugar level becomes equal to or more than a predetermined value and transmits an operation command to increase the injection dose of the fluid to the fluid injection apparatus via the first communicating section.

With such a fluid injection system, even when the apparatus wearer becomes hyperglycemia, it is possible to increase the injection dose of the chemical and thereby use the apparatus safely.

First Embodiment

In a first embodiment, a case in which insulin is administered to a diabetic patient by using a fluid injection system 1 will be described.

Figure 1:
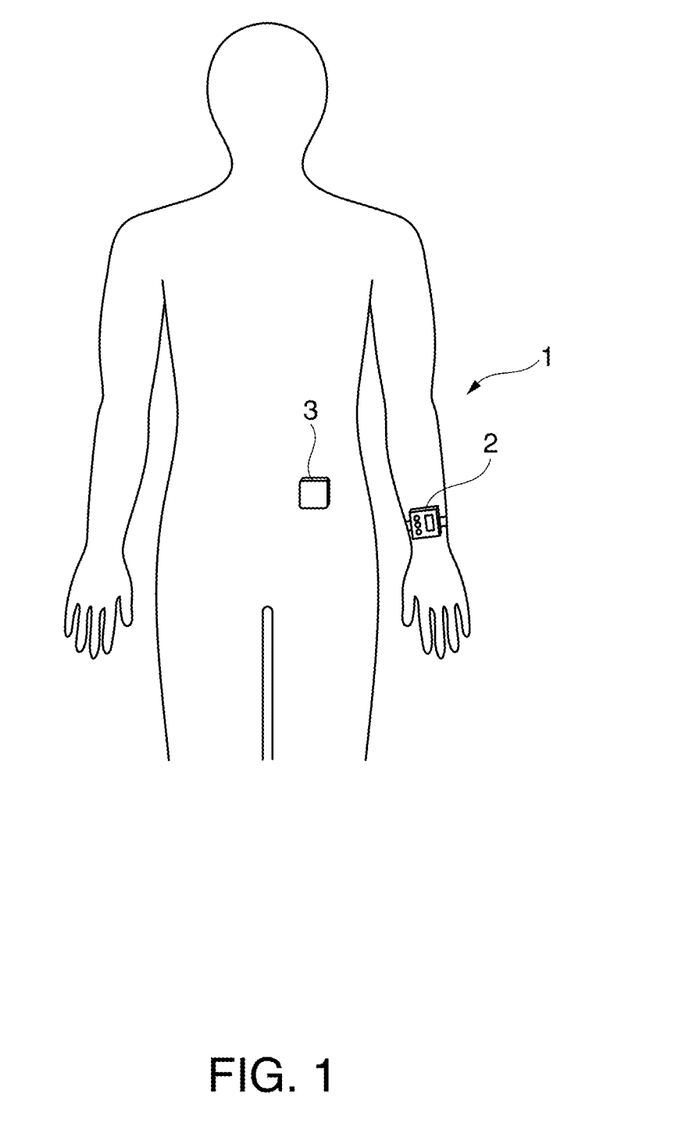
FIG. 1 shows a state in which a fluid injection system 1 is attached to a human body.

FIG. 1 shows a state in which the fluid injection system 1 is attached to a human body. As shown in FIG. 1, the fluid injection system 1 includes an operating apparatus 2 and a fluid injection apparatus 3. The operating apparatus 2 is used by being attached to a wrist, and the fluid injection apparatus 3 is used by being attached to a trunk of the body. Specifically, insulin is stored in the fluid injection apparatus 3, and, when an operation command to start medication is entered into the operating apparatus 2 before meal, insulin is injected into the human body from the fluid injection apparatus 3.

Configuration of the Fluid Injection System 1

Figure 2:
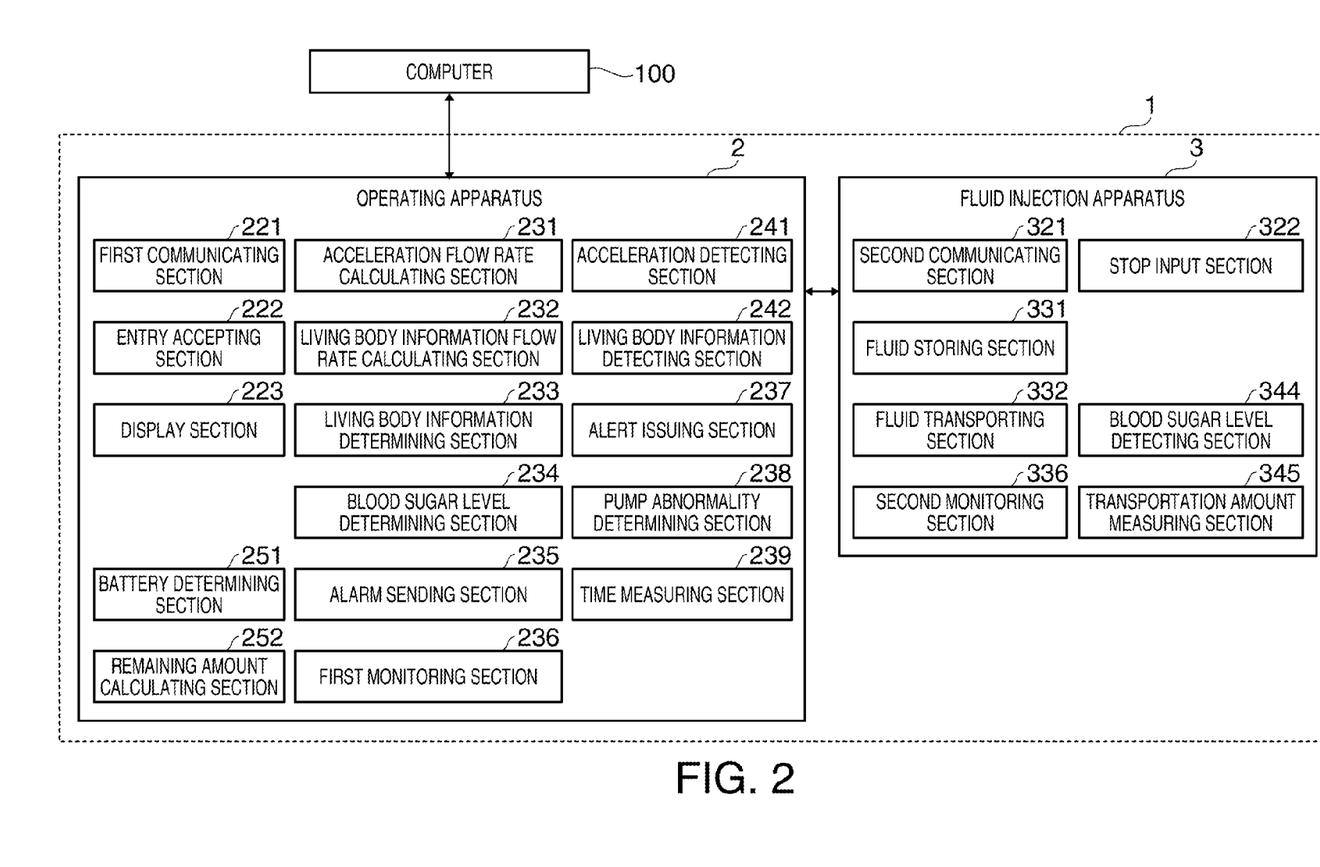
FIG. 2 is a block configuration diagram showing the function of the fluid injection system 1.

FIG. 2 is a block configuration diagram showing the function of the fluid injection system 1. The operating apparatus 2 includes a first communicating section 221, an entry accepting section 222, a display section 223, an acceleration flow rate calculating section 231, a living body information flow rate calculating section 232, a living body information determining section 233, a blood sugar level determining section 234, an alarm sending section 235, a first monitoring section 236, an alert issuing section 237, a pump abnormality determining section 238, a time measuring section 239, an acceleration detecting section 241, a living body information detecting section 242, a battery determining section 251, and a remaining amount calculating section 252. The fluid injection apparatus 3 includes a second communicating section 321, a stop input section 322, a fluid storing section 331, a fluid transporting section 332, and a second monitoring section 336. Incidentally, the operating apparatus 2 is controlled by a first controller (not shown) provided in the operating apparatus 2, and the fluid injection apparatus 3 is controlled by a second controller (not shown) provided in the fluid injection apparatus 3.

The first communicating section 221 performs wireless communication with the fluid injection apparatus 3 and performs wireless communication with an external computer 100.

The entry accepting section 222 is an operation button, for example, and accepts operation commands to start and stop insulin medication from a patient who uses the fluid injection system 1.

The acceleration detecting section 241 is a gyro sensor, for example, and detects the acceleration. The acceleration flow rate calculating section 231 determines whether or not an apparatus wearer performs exercise by which the apparatus wearer consumes a large amount of energy (hereinafter referred to as "heavy exercise") based on the acceleration detected by the acceleration detecting section 241. When the apparatus wearer performs heavy exercise, the acceleration flow rate calculating section 231 determines the exercise intensity and calculates the injection dose of insulin based on the exercise intensity. That is, when the exercise intensity is high, the acceleration flow rate calculating section 231 reduces the injection dose of insulin; when the exercise intensity is low, the acceleration flow rate calculating section 231 increases the injection dose of insulin.

The living body information detecting section 242 detects living body information such as a pulse, a blood pressure, and a body temperature. The living body information flow rate calculating section 232 determines whether or not the apparatus wearer performs heavy exercise based on the living body information detected by the living body information detecting section 242. Specifically, when there are an increase in pulse rate and a rise in blood pressure, body temperature, and the like, the living body information flow rate calculating section 232 determines that the apparatus wearer starts heavy exercise. When the apparatus wearer performs heavy exercise, the living body information flow rate calculating section 232 determines the exercise intensity based on the living body information, and calculates the injection dose of insulin based on the exercise intensity. That is, when the exercise intensity is high, the living body information flow rate calculating section 232 reduces the injection dose of insulin; when the exercise intensity is low, the living body information flow rate calculating section 232 increases the injection dose of insulin.

Moreover, the living body information determining section 233 determines whether or not the apparatus wearer is in poor physical condition based on the living body information detected by the living body information detecting section 242. That is, the living body information determining section 233 makes a determination based on whether or not the values of the pulse, the blood pressure, the body temperature, and the like are equal to or more than their respective lower limits at which the apparatus wearer can be regarded as being in normal condition. For example, when the values of the pulse, the blood pressure, the body temperature, and the like are less than their respective lower limits, there is a possibility that abnormalities such as hypoglycemia occur in the body, and the living body information determining section 233 determines the presence or absence of such abnormalities.

The blood sugar level determining section 234 determines whether or not the apparatus wearer is in a state of hypoglycemia based on the blood sugar level detected by a blood sugar level detecting section 344 which will be described later. That is, the blood sugar level determining section 234 makes a determination based on whether or not the blood sugar level is equal to or less than a normal level range of the apparatus wearer.

The alarm sending section 235 produces an alarm tone or vibration when the acceleration flow rate calculating section 231 or the living body information flow rate calculating section 232 determines that the apparatus wearer performs heavy exercise, the living body information determining section 233 determines that something is wrong with the body of the apparatus wearer, or the blood sugar level determining section 234 determines that the apparatus wearer is in a state of hypoglycemia. Incidentally, the alarm sending section 235 may produce an alarm tone or vibration corresponding to each determination.

The first monitoring section 236 monitors whether or not the controller (not shown) controlling the fluid injection apparatus 3 is operating normally. Specifically, the first monitoring section 236 determines whether or not the second controller is operating normally based on whether or not the first monitoring section 236 receives a response from the second controller to a signal transmitted to the second controller of the fluid injection apparatus 3 from the first monitoring section 236 at predetermined time intervals. In this way, the first monitoring section 236 monitors the second controller.

The alert issuing section 237 produces a beep tone or vibration when the first monitoring section 236 determines that something is wrong with the second controller. Moreover, the alert issuing section 237 also produces a beep tone or vibration when the second monitoring section 336, which will be described later, determines that something is wrong with the second controller. Incidentally, the beep tone or vibration is louder than the alarm tone or vibration described above, and strongly calls the apparatus wearer's attention.

The pump abnormality determining section 238 determines whether or not something is wrong with the fluid transporting section 332 of the fluid injection apparatus 3. Specifically, the pump abnormality determining section 238 determines whether or not something is wrong with the fluid transporting section 332 based on whether or not there is a correspondence between the operation command which the entry accepting section 222 has accepted and the transportation amount of insulin measured by a transportation amount measuring section 345 which will be described later.

The time measuring section 239 measures time.

The battery determining section 251 determines whether or not the operating apparatus 2 and the fluid injection apparatus 3 have a sufficient remaining battery level.

The remaining amount calculating section 252 calculates the remaining amount of insulin stored in the fluid storing section 331 based on the transportation amount of insulin measured by the transportation amount measuring section 345 which will be described later and the amount of insulin stored in the fluid storing section 331 which will be described later.

The second communicating section 321 performs wireless communication with the operating apparatus 2.

The stop input section 322 is a stop button which stops the operation of the fluid injection apparatus 3. The stop button is provided with a lid (not shown) for protecting the stop button and preventing the stop button from being pressed accidentally.

The fluid storing section 331 is a tank, for example, and stores insulin inside it.

The fluid transporting section 332 has a pump and a tube which transport a fluid, and transports insulin into the body of the apparatus wearer from the fluid storing section 331.

The second monitoring section 336 is a control section provided independently of the second controller. The second monitoring section 336 regularly performs communication with the second controller of the fluid injection apparatus 3 and determines whether or not the second controller is operating normally. When the second monitoring section 336 determines that the second controller is not operating normally, the second monitoring section 336 transmits, to the first controller, information indicating that the second controller is not operating normally.

The blood sugar level detecting section 344 regularly detects the blood sugar level of the apparatus wearer. The blood sugar level detected by the blood sugar level detecting section 344 is transmitted to the operating apparatus 2 via the second communicating section 321.

The transportation amount measuring section 345 measures the transportation amount of insulin injected to the human body of the apparatus wearer from the fluid storing section 331. The transportation amount of insulin measured by the transportation amount measuring section 345 is transmitted to the operating apparatus 2 via the second communicating section 321.

The display section 223 is a liquid crystal display, for example, and displays, in addition to the acceleration detected by the acceleration detecting section 241, the living body information detected by the living body information detecting section 242, and the blood sugar level detected by the blood sugar level detecting section 344, the determination results obtained by the acceleration flow rate calculating section 231, the living body information flow rate calculating section 232, the living body information determining section 233, and the blood sugar level determining section 234. The display section 223 displays data of the transportation amount of insulin at given times, the date transmitted from the fluid injection apparatus 3, and the remaining amount of insulin in the fluid storing section 331, the remaining amount calculated by the remaining amount calculating section 252. When the fluid injection apparatus 3 administers insulin, the display section 223 displays the time it takes for the fluid injection apparatus 3 to finish administration of insulin.

Chemical Injection Operation

When people take a meal, the sugar is introduced to the body, which causes a rise in blood sugar level. Thus, diabetic patients have to control their blood sugar levels by receiving a large amount of insulin at meals. On the other hand, when people perform heavy exercise, they consume energy, which causes a reduction in blood sugar level. Thus, the diabetic patients require a reduction in dose of insulin or stop administration of insulin when they perform heavy exercise. The fluid injection system 1 injects an appropriate amount of insulin into the apparatus wearer in such a manner as to meet such requirements.

Figure 3:
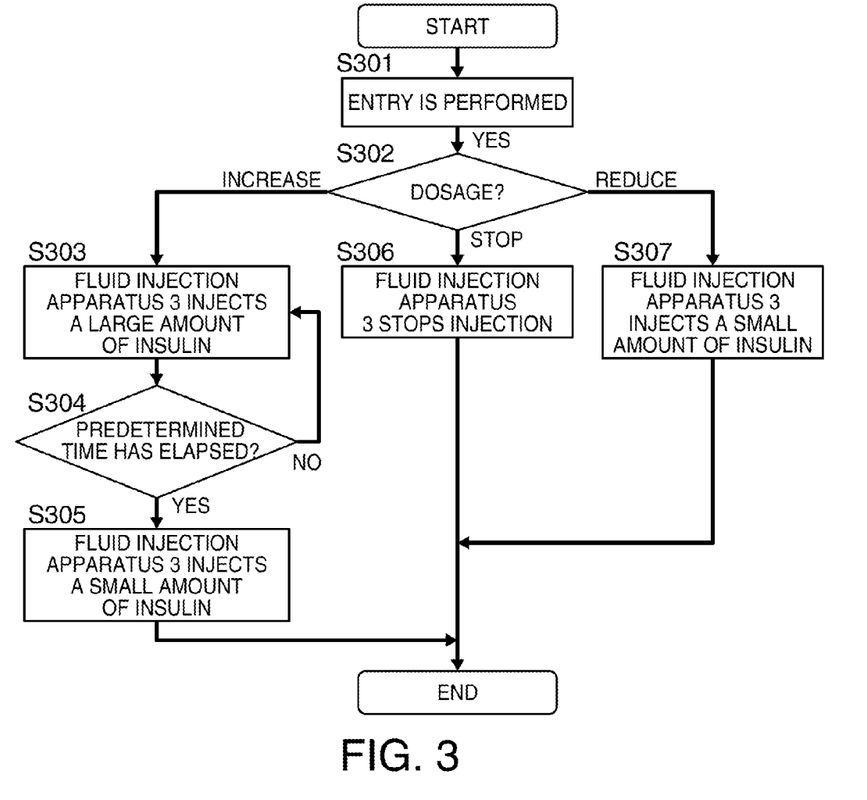
FIG. 3 is a flow diagram showing the procedure performed by the fluid injection system 1 to inject a chemical.

FIG. 3 is a flow diagram showing the procedure performed by the fluid injection system 1 to inject a chemical. Based on FIG. 3, the chemical injection procedure of the fluid injection system 1 will be described.

First, when an entry operation from an operator is performed on the entry accepting section 222 (S301), it is determined whether the entry operation is an operation instruction to increase the dosage of insulin, an operation instruction to reduce the dosage of insulin, or an operation instruction to stop administration of insulin (S302).

If the entry operation is an operation instruction to increase the dosage of insulin (S302: "INCREASE"), the first communicating section 221 of the operating apparatus 2 transmits, to the fluid injection apparatus 3, an operation command to make the fluid injection apparatus 3 inject a large amount of insulin, and the fluid injection apparatus 3 injects a large amount of insulin into the human body of the apparatus wearer (S303). Then, if a predetermined time has not elapsed (S304: NO), the fluid injection apparatus 3 continuously injects insulin in S303. If a predetermined time has elapsed (S304: YES), the fluid injection apparatus 3 continuously injects a small amount of insulin into the human body of the apparatus wearer (S305).

If the entry operation is an operation instruction to stop administration of insulin (S302: "STOP"), the first communicating section 221 transmits, to the fluid injection apparatus 3, an operation command to make the fluid injection apparatus 3 stop injection of insulin, and the fluid injection apparatus 3 stops injection of insulin (S306).

If the entry operation is an operation instruction to reduce the dosage of insulin (S302: "REDUCE"), the first communicating section 221 transmits, to the fluid injection apparatus 3, an operation command to make the fluid injection apparatus 3 inject a small amount of insulin, and the fluid injection apparatus 3 continuously injects a small amount of insulin into the human body of the apparatus wearer (S307).

Monitoring of the State of the Apparatus Wearer

When the acceleration flow rate calculating section 231 determines that the apparatus wearer is performing heavy exercise, the acceleration flow rate calculating section 231 transmits, to the fluid injection apparatus 3 via the first communicating section 221, an operation command to make the fluid injection apparatus 3 stop injection of insulin, and the fluid injection apparatus 3 stops injection of insulin. Moreover, the alarm sending section 235 produces an alarm tone or vibration, and the display section 223 displays a message saying that injection of insulin is stopped because the apparatus wearer is performing heavy exercise.

When the living body information flow rate calculating section 232 determines that the apparatus wearer is performing heavy exercise, the living body information flow rate calculating section 232 transmits, to the fluid injection apparatus 3 via the first communicating section 221, an operation command to make the fluid injection apparatus 3 stop injection of insulin, and the fluid injection apparatus 3 stops injection of insulin. Moreover, the alarm sending section 235 produces an alarm tone or vibration, and the display section 223 displays a message saying that injection of insulin is stopped because the apparatus wearer is performing heavy exercise.

Moreover, when the living body information determining section 233 detects an abnormality, the alarm sending section 235 produces an alarm tone or vibration, and the display section 223 displays the living body information and a message saying that the apparatus wearer is in a state of hypoglycemia. In addition, the operating apparatus 2 transmits, to the external computer 100, information indicating that something is wrong with the apparatus wearer.

When the blood sugar level determining section 234 determines that the apparatus wearer is in a state of hypoglycemia, the blood sugar level determining section 234 transmits an operation command to stop injection of insulin to the fluid injection apparatus 3 via the first communicating section 221, and the fluid injection apparatus 3 stops injection of insulin. Moreover, the alarm sending section 235 produces an alarm tone or vibration, and the display section 223 displays the blood sugar level and a messages saying that injection of insulin is stopped.

On the other hand, when the blood sugar level determining section 234 determines that the apparatus wearer is in a state of hyperglycemia, the blood sugar level determining section 234 transmits an operation command to increase the injection dose of insulin to the fluid injection apparatus 3 via the first communicating section 221, and the fluid injection apparatus 3 increases the injection dose of insulin. Moreover, the alarm sending section 235 produces an alarm tone or vibration, and the display section 223 displays the blood sugar level and a message saying that the injection dose of insulin is increased.

Monitoring of the Fluid Injection Apparatus

The first monitoring section 236 regularly transmits a signal to the second controller of the fluid injection apparatus 3 at predetermined time intervals, and determines whether or not the second controller is operating normally based on whether or not the first monitoring section 236 receives a response from the second controller to the signal thus transmitted. If the first monitoring section 236 determines that the second controller is not operating normally, the alert issuing section 237 produces a beep tone or vibration.

The second monitoring section 336 regularly transmits a signal to the second controller, and determines whether or not the second controller is operating normally. If the second monitoring section 336 determines that the second controller is not operating normally, the second monitoring section 336 transmits the determination result to the operating apparatus 2 via the second communicating section 321, and the alert issuing section 237 produces a beep tone or vibration.

The pump abnormality determining section 238 determines whether or not something is wrong with the fluid transporting section 332 based on whether or not there is a correspondence between the operation command which the entry accepting section 222 has accepted and the transportation amount of insulin measured by the transportation amount measuring section 345 which will be described later. If the pump abnormality determining section 238 determines that something is wrong with the fluid transporting section 332, the alert issuing section 237 produces a beep tone or vibration.

The battery determining section 251 determines whether or not the operating apparatus 2 and the fluid injection apparatus 3 have a sufficient remaining battery level. For example, the battery determining section 251 determines that there is not a sufficient remaining battery level when the remaining battery level is lower than a predetermined percentage of a battery capacity. When the battery determining section 251 determines that the operating apparatus 2 or the fluid injection apparatus 3 does not have a sufficient remaining battery level, the alert issuing section 237 produces a beep tone or vibration.

Effectiveness of the Fluid Injection System

Figure 4:
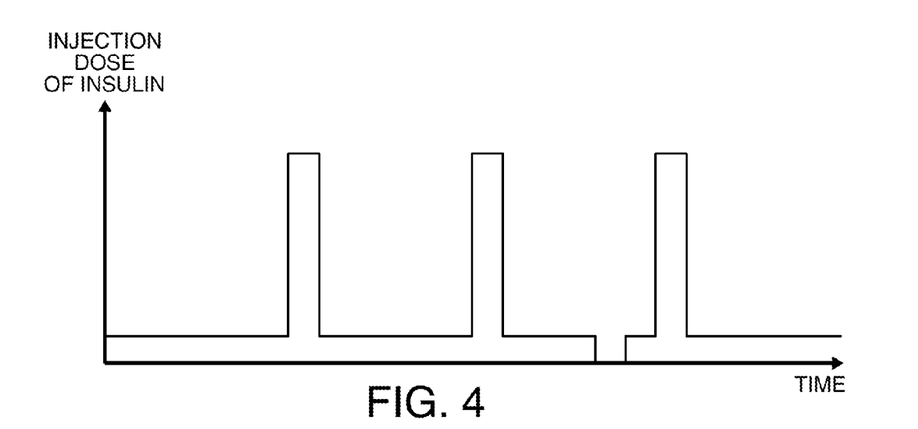
FIG. 4 is a graph showing the injection dose of insulin required by a diabetic patient in chronological order.

FIG. 4 is a graph showing the injection dose of insulin required by a diabetic patient in chronological order. As shown in FIG. 4, the diabetic patient requires a large amount of insulin during meal and before and after meal, and requires a small amount of insulin during sleep and rest. Moreover, the diabetic patient does not require insulin when the diabetic patient consumes a large amount of energy by exercise or the like. As described above, since the required amount of insulin is changed according to the life situation of the apparatus wearer, it is necessary to operate or control the operation of the fluid injection system 1 according to the required amount of insulin.

The fluid injection system 1 includes the fluid injection apparatus 3 which is attached to a trunk of a human body and injects a fluid into the human body and the operating apparatus 2 which is attached to a wrist of the human body and remotely controls the fluid injection apparatus 3. The operating apparatus 2 has the entry accepting section 222 which accepts an entry of an operation command to the fluid injection apparatus 3 and the first communicating section 221 which transmits the operation command to the fluid injection apparatus 3. The fluid injection apparatus 3 has the second communicating section 321 which receives the operation command, the fluid storing section 331 which stores the fluid, and the fluid transporting section 332 which transports the fluid from the fluid storing section 331 and injects the fluid into the human body based on the operation command. As a result, the apparatus wearer of the fluid injection system 1 can operate the fluid injection apparatus without getting partially undressed.

Specifically, with the existing fluid injection apparatus, a diabetic patient has to receive an insulin injection at every meal and directly operates a fluid injection apparatus by getting partially undressed at each medication to operate the fluid injection apparatus. That is, getting partially undressed at every meal makes the apparatus wearer feel unpleasant in terms of public manner, and inflicts psychological suffering on the apparatus wearer, such as a fear of being exposed as a diabetic patient. However, the fluid injection system 1 allows the apparatus wearer to control the fluid injection apparatus 3 remotely by the operating apparatus 2 attached to the apparatus wearer's wrist as if checking the time on a wrist watch. This eliminates not only the need to get partially undressed but also the possibility of being exposed as a diabetic patient. In this way, the fluid injection system 1 can release the diabetic patient from psychological suffering.

Moreover, in the fluid injection system 1, the operating apparatus 2 has the living body information detecting section 242 which detects the living body information of the human body and the living body information flow rate calculating section 232 which calculates, based on the living body information, the fluid flow rate of the fluid which is injected by the fluid injection apparatus 3. This makes it possible to calculate the dosage of insulin based on the living body information and thereby administer an appropriate amount of insulin to the apparatus wearer.

Specifically, when there are an increase in pulse rate and a rise in blood pressure and body temperature, it can be determined that the apparatus wearer performs heavy exercise or the like. When the apparatus wearer performs heavy exercise, the energy such as sugar in the body is consumed, which reduces the need to inject insulin. Therefore, with the fluid injection system 1, when there are an increase in pulse rate and a rise in blood pressure and body temperature, it is possible to reduce the injection dose of insulin or stop injection of insulin.

On the other hand, when there are a decrease in pulse rate and a fall in blood pressure and body temperature, it can be determined that the apparatus wearer is in a dangerous state of hypoglycemia. When the apparatus wearer is in a state of hypoglycemia, insulin must not be injected. Therefore, with the fluid injection system 1, when there are a decrease in pulse rate and a fall in blood pressure and body temperature, it is possible to stop injection of insulin.

Moreover, in the fluid injection system 1, the operating apparatus 2 includes the acceleration detecting section 241 which detects the acceleration of the operating apparatus 2 and the acceleration flow rate calculating section 231 which calculates the fluid flow rate based on the acceleration. This makes it possible to calculate the dosage of insulin based on the exercise situation of the apparatus wearer and thereby administer an appropriate amount of insulin to the apparatus wearer. That is, when the apparatus wearer performs heavy exercise, the energy such as sugar in the body is consumed, which reduces the need to inject insulin. Therefore, with the fluid injection system 1, when the apparatus wearer performs heavy exercise, it is possible to reduce the injection dose of insulin or stop injection of insulin.

In addition, in the fluid injection system 1, the fluid injection apparatus 3 includes the second controller which controls the fluid transporting section 332 and the second monitoring section 336 which monitors the second controller, and the operating apparatus 2 includes the first monitoring section 236 which monitors the second controller and the alert issuing section 237 which issues an alert when the first monitoring section 236 or the second monitoring section 336 detects an abnormality in the second controller. Therefore, when something is wrong with the second controller of the fluid injection apparatus 3, it is possible to inform the apparatus wearer of the abnormality without delay. Even when something is wrong with the second controller, it is difficult to determine whether or not something is wrong with the second controller by just looking at the second controller. However, injecting an inappropriate amount of insulin due to the abnormality in the second controller causes life-threatening results. The fluid injection system 1 provides a double surveillance system formed of the second monitoring section 336 inside the fluid injection apparatus 3 and the first monitoring section 236 from the outside of the fluid injection apparatus 3, making it possible to improve the safety in use.

Moreover, in the fluid injection system 1, the fluid injection apparatus 3 includes the transportation amount measuring section 345 which measures the fluid flow rate of the fluid transported by the fluid transporting section 332, and the operating apparatus 2 includes the pump abnormality determining section 238 which determines whether or not something is wrong with the fluid transporting section 332 based on the operation command and the data on the fluid flow rate and the alarm sending section 235 which sends an alarm when the pump abnormality determining section 238 detects an abnormality. As a result, when something is wrong with the fluid transporting section 332 of the fluid injection apparatus 3, it is possible to inform the apparatus wearer of the abnormality without delay and improve the safety in use. If the fluid transporting section 332 does not operate due to a failure, insulin is not injected appropriately, endangering the apparatus wearer's life. Furthermore, if the fluid transporting section 332 continuously injects a large amount of insulin due to a failure, the apparatus wearer's life is endangered. However, with the fluid injection system 1, it is possible to find out the abnormality in the fluid transporting section 332 by the pump abnormality determining section 238 and inform the apparatus wearer of the abnormality before the situation becomes serious.

Furthermore, in the fluid injection system 1, the fluid injection apparatus 3 includes the blood sugar level detecting section 344 which detects the blood sugar level of the human body, and the operating apparatus 2 includes the blood sugar level determining section 234 which determines that the apparatus wearer is in a state of hypoglycemia when the blood sugar level is less than a predetermined value and transmits, to the fluid injection apparatus 3 via the first communicating section 221, an operation command to stop injection of fluid. As a result, even when the apparatus wearer becomes hypoglycemia, it is possible to stop injection of insulin and allow the apparatus to be used safely. For example, even when the apparatus wearer becomes hypoglycemia without a subjective symptom or the apparatus wearer becomes unconscious due to hypoglycemia or the like, it is possible to stop injection of insulin.

Moreover, in the fluid injection system 1, the blood sugar level determining section 234 determines that the apparatus wearer is in a state of hyperglycemia when the blood sugar level is equal to or more than a predetermined value, and transmits, to the fluid injection apparatus 3 via the first communicating section 221, an operation command to increase the injection dose of fluid. As a result, even when the apparatus wearer becomes hyperglycemia, it is possible to increase the injection dose of insulin and allow the apparatus to be used safely. For example, even when the apparatus wearer forgets to perform operation to inject insulin at meals, it is possible to prevent a rise in blood sugar level by increasing the injection dose of insulin.

In addition, in the fluid injection system 1, the remaining amount of insulin is displayed in the display section 223 of the operating apparatus 2 attached to a wrist. As a result, the apparatus wearer can check the remaining amount of insulin easily without getting partially undressed.

Furthermore, in the fluid injection system 1, data on insulin injection, the data accumulated in the fluid injection system 1, can be transmitted to the external computer 100. This makes it possible for a doctor who treats the apparatus wearer to get data in his/her computer, the data on the insulin injection situation and the blood sugar level, the pulse, the body temperature, and the blood pressure corresponding to the insulin injection situation, and use the data for treatment of the apparatus wearer.

Moreover, in the fluid injection system 1, the stop input section 322 of the fluid injection apparatus 3 is protected by the lid. This reduces the risk of operating the stop input section 322 accidentally.

Other Embodiments

Although the invention has been described by way of an embodiment, the embodiment described above is merely intended to make the invention more easily understandable, and is not meant to limit the scope of the invention in any way. It is to be understood that many modifications and variations are possible within the spirit of the invention, and the invention includes the equivalent thereof. In particular, the embodiments described below are also included in the invention.

In the first embodiment, the fluid injection apparatus 3 is used by being attached to a trunk of the body. However, the fluid injection apparatus 3 may be used by being attached to, in addition to a trunk of the body, an upper arm or a leg.

Moreover, in the first embodiment, the fluid is insulin. However, the fluid is not limited to insulin, and any fluid may be used as long as the fluid is a chemical or saline, has fluidity, and is injected into a human body.

In FIG. 3, the injection dose of insulin is changed in three levels: a large amount of insulin, a small amount of insulin, and stopping injection of insulin; however, it is also possible to regulate the injection dose of insulin minutely by changing the injection dose of insulin in more than three levels. For example, the injection dose of insulin at meals may be determined by the apparatus wearer according to the size of a meal. This makes it possible to inject a more appropriate amount of insulin.

The fluid injection apparatus 3 stops injection of insulin based on the calculation result obtained by the acceleration flow rate calculating section 231 or the living body information flow rate calculating section 232. However, the alarm sending section 235 may inform the apparatus wearer of an abnormality by producing an alarm tone or vibration without stopping injection of insulin. That is, the operation related to the injection dose of insulin may be performed eventually based on the judgment of the apparatus wearer. This makes it possible to prevent the apparatus wearer from forgetting to inject insulin, and allows the apparatus wearer to use the apparatus with a sense of security because insulin is not injected without the apparatus wearer's consent.

The operating apparatus 2 may store data on an operation manual of the fluid injection system 1, and the display section 223 may display the operation manual. This makes it possible for the apparatus wearer to view the operation manual readily and operate the fluid injection system 1 in an appropriate manner.

The display section 223 may display the time measured by the time measuring section 239. Moreover, the alarm sending section 235 may produce an alarm tone at a predetermined time and inform the apparatus wearer that it is time to inject insulin. For example, by registering a mealtime in the operating apparatus 2 in advance, even when the apparatus wearer forgets to perform operation to inject insulin at meals, the apparatus wearer can remember operation to inject insulin when the alarm tone is produced and perform the operation.

The acceleration detecting section 241 is provided in the operating apparatus 2; however, the acceleration detecting section 241 may be provided in the fluid injection apparatus 3 or may be provided in both the operating apparatus 2 and the fluid injection apparatus 3. When the acceleration detecting section 241 is provided in both the operating apparatus 2 and the fluid injection apparatus 3, it is possible to detect the acceleration of the apparatus wearer more accurately.

What is claimed is:

1. A fluid injection apparatus, comprising:
a fluid injection unit which is adapted to be attached to a human body and injects medical fluid into the human body in response to an operation command, wherein the fluid injection unit includes:
a first wireless communicating section configured to receive an operation command and transmit a transportation amount of the medical fluid injected by the fluid injection unit, and
a storing section co9nfigured to store the medical fluid, and
a control unit that remotely controls the fluid injection unit, wherein the control unit is adapted to be attached to the human body and wherein the control unit includes:
an entry accepting section configured to receive the operation command while the control unit is attached to the human body;
an abnormality determining section determining an abnormality with the fluid injection unit based upon whether there is a correspondence between the operation command and the transportation amount, and a second wireless communicating section configured to transmit the operation command to the first wireless communicating section while the control unit is attached to the human body.

2. The fluid injection apparatus according to claim 1, wherein the operation command includes a command to start the fluid injection and a command to stop the fluid injection.

3. The fluid injection apparatus according to claim 1, wherein the medical fluid is an antidiabetic drug.

4. The fluid injection apparatus according to claim 1, wherein the control unit comprises a first monitoring section.

5. The fluid injection apparatus according to claim 4, wherein the fluid injection unit comprises a controller and a second monitoring section.

6. The fluid injection apparatus according to claim 5, wherein the second monitoring section monitors the controller and wherein the first monitoring section monitors the controller.

7. The fluid injection apparatus according to claim 6, wherein an alert is issued when the first monitoring section or the second monitoring section detects an abnormality in the controller.

8. The fluid injection apparatus of according to claim 5, wherein the control unit includes an alert issuing section.

9. The fluid injection apparatus according to claim 8, wherein the alert issuing section issues an alert based upon the abnormality determining section determining the abnormality with the fluid injection unit.

10. The fluid injection apparatus according to claim 8, wherein the alert issuing section issues an alert based upon an abnormality detected by the second monitoring section.

\* \* \* \* \*